United States Patent
Wollin

(10) Patent No.: US 7,238,664 B2
(45) Date of Patent: Jul. 3, 2007

(54) COMPOSITION COMPRISING A PULMONARY SURFACTANT AND A PDE5 INHIBITOR FOR THE TREATMENT OF LUNG DISEASES

(75) Inventor: Stefan-Lutz Wollin, Meersburg (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/560,116

(22) PCT Filed: Jun. 15, 2004

(86) PCT No.: PCT/EP2004/051120

§ 371 (c)(1),
(2), (4) Date: Dec. 9, 2005

(87) PCT Pub. No.: WO2004/110450

PCT Pub. Date: Dec. 23, 2004

(65) Prior Publication Data

US 2006/0148693 A1    Jul. 6, 2006

(30) Foreign Application Priority Data

Jun. 16, 2003    (EP) ................................. 03013615

(51) Int. Cl.
*A61K 31/00* (2006.01)
(52) U.S. Cl. .................... 514/12; 514/252.16
(58) Field of Classification Search ............... None
See application file for complete search history.

(56) References Cited

U.S. PATENT DOCUMENTS 5,891,844 A    4/1999 Häfner

FOREIGN PATENT DOCUMENTS

| EP | 1 223 170 A1 | 7/2002 |
| WO | 96/09831 A2 | 4/1996 |
| WO | 98/35683 A1 | 8/1998 |
| WO | 99/66926 A1 | 12/1999 |
| WO | 00/27360 A1 | 5/2000 |
| WO | 01/58423 A1 | 8/2001 |
| WO | WO 01/76619 * | 10/2001 |
| WO | 03/011316 A1 | 2/2003 |

OTHER PUBLICATIONS

Wilkins P. A. et al., "Acute Respiratory Failure:Diagnosis, Monitoring Techniques, and Therapeutics", Mar. 2003, Clinical Techniques in Equine Practice, vol. 2:56-66.*
Bernard, G.R., et al., "Report of the American-European consensus conference on ARDS: definitions, mechanisms, relevant outcomes and clinical trial coordination", *Intensive Care Med*, vol. 20, pp. 225-232, (1994).
Ghofrani, H.A., et al., "Sildenafil for treatment of lung fibrosis and pulmonary hypertension: a randomised controlled trial", *The Lancet*, vol. 360, pp. 895-900, (2002).
Griese, M., "Pulmonary surfactant in health and human lung diseases: state of the art", *Eur Respir J*, vol. 13, pp. 1455-1476, (1999).
Hohlfeld, J., et al., "The role of pulmonary surfactant in obstructive airways disease", *Eur Respir J*, vol. 10, pp. 482-491, (1997).
Lewis, J.F., et al., "Role of exogenous surfactant in acute lung injury", *Crit Care Med*, vol. 31, No. 4, pp. S324-S328, (2003).
Santos, S., et al., "Characterization of pulmonary vascular remodeling in smokers and patients with mild COPD", *Eur Respir J*, vol. 19, pp. 632-638, (2002).
Suttorp, N., et al., "Phosphodiesterasen-Inhibition und pulmonale Strombahn—ein neuer Therapieansatz?", *Atemwegs und Lungenkrankheiten*,, vol. 22, pp. 560-566, (1996). (ABSTRACT).
Twohig, H.J., et al., "Sildenafil Decreases Arterial Oxygen Levels in Patients with Chronic Obstructive Pulmonary Disease", *Thorax*, vol. 55, pp. A40, (2000).
Walmrath, D., et al., "Bronchoscopic Surfactant Administration in Patients with Severe Adult Respiratory Distress Syndrome and Sepsis", *Am J Respir Care Med*, vol. 154, pp. 57-62, (1996).
Zhao, L., et al., "Sildenafil Inhibits Hypoxia-Induced Pulmonary Hypertension", *Circulation*, vol. 104, pp. 424-428, (2001).

* cited by examiner

*Primary Examiner*—Cecilia J. Tsang
*Assistant Examiner*—Hemant Khanna
(74) *Attorney, Agent, or Firm*—The Nath Law Group; Joshua B. Goldberg; Sheldon M. McGee

(57) ABSTRACT

The invention relates to the combined administration of a pulmonary surfactant and a PDE5 inhibitor for the treatment of a disease in which pulmonary surfactant malfunction and/or phosphodiesterase 5 (PDE5) activity is detrimental.

3 Claims, No Drawings

COMPOSITION COMPRISING A PULMONARY SURFACTANT AND A PDE5 INHIBITOR FOR THE TREATMENT OF LUNG DISEASES

FIELD OF APPLICATION OF THE INVENTION

The invention relates to the combination of certain known active compounds for therapeutic purposes. The compounds used in the combination according to this invention are known pulmonary surfactants and known active compounds from the phosphodiesterase 5 (PDE5) inhibitor class. Their combined use in the sense according to this invention for therapeutic purposes has not yet been described in prior art.

PRIOR ART

In the healthy lung of humans both at rest and during exercise there are always areas of good and poor or absolutely no ventilation existing simultaneously side by side (ventilation inhomogeneity). An as yet unknown mechanism ensures that there is little or no perfusion of the capillaries adjacent to alveoli with little or no ventilation. This occurs in order to minimize inefficient perfusion of areas of the lung which are not involved in gas exchange. During bodily exercise, the distribution of ventilation changes (recruitment of new alveoli) and there is increased perfusion of the relevant capillary bed. Conversely, when there is less ventilation due to physiological or pathological processes (airway obstruction), the capillary flow are reduced through vasoconstriction. This process is referred to as "hypoxic vasoconstricton" (Euler-Lijestrand mechanism).

When this adaptation mechanism of ventilation and perfusion is impaired ("mismatch"), there may, despite adequate ventilation and normal perfusion of the lungs, be a more or less pronounced collapse of the gas exchange function, which can be compensated only inadequately despite a further increase in ventilation or perfusion. Under these conditions there are regions which are not ventilated but are well perfused (shunting) and those which are well ventilated but not perfused (dead space ventilation). The consequences of this ventilation/perfusion mismatch are hypoxaemia (deterioration in gas exchange with decrease in the oxygen content of the patient's blood), wasted perfusion (uneconomical perfusion of unventilated areas) and wasted ventilation (uneconomical ventilation of poorly perfused areas).

In patients with inflammatory and degenerative lung disorders such as, for example, chronic obstructive pulmonary disease (COPD), bronchitis, bronchial asthma, pulmonary fibroses, emphysema, interstitial pulmonary disorders and pneumonias there is observed to be partial or global respiratory failure. A cause is inadequate adaptation of the intrapulmonary perfusion conditions to the inhomogeneous pattern of the distribution of ventilation.

COPD patients suffer from pulmonary alterations, i.e. changes of the airways and pulmonary vessels, and from extra-pulmonary alterations. Airways are obstructed due to inflammation and mucus hypersecretion with coexistent impaired mucus clearance. Alveolar walls are destructed resulting in emphysema. The limited airflow and the loss of respiratory epithelium results in impaired oxygenation. Pulmonary blood circulation is impaired due to vascular remodelling with smooth muscle cell proliferation, elastin and collagen deposition in the thickened intima [Santos S et al. Eur Respir J 2002 19: 632-8] Characterization of pulmonary vascular remodelling in smokers and patients with mild COPD.] and due to a ventilation/perfusion mismatch. The mismatch derives from the effect of vasoactive (inflammatory) mediators prevailing over the physiological adaptation mechanism and in part from structural changes of the lung capillaries which develop during the disease progression. This effect is particularly evident during exercise and when the oxygen demand is increased and it is manifested by dyspnoea (hypoxia) and limitation of body performance. Up to now a curative therapy for COPD is not available. In use are anti-cholinergic drugs (ipratropium bromide, tiotropium bromide and oxitropium bromide) and short- and long-acting β-adrenoreceptor-agonists (salmeterol, terbutalin-sulphate).

ARDS (Adult Respiratory Distress Syndrome) patients also suffer from a ventilation/perfusion mismatch resulting in collapse of the gas exchange function. ARDS is a descriptive expression which is applied to a large number of acute, diffuse infiltrative pulmonary lesions of differing etiology associated with a severe gas exchange disorder (In particular arterial hypoxemia) [G. R. Bernard et al.: Report of the American-European consensus conference on ARDS: definitions, mechanisms, relevant outcomes and clinical trial coordination; Intensive Care Medicine, 1994, 20/225-232]. The expression ARDS is also used for IRDS (infant Respiratory Distress Syndrome) because of numerous common clinical and pathological features. While in the case of IRDS the lung surfactant deficiency is caused by premature birth, the lung surfactant malfunction in the case of ARDS is caused by the disease of the lung based on differing etiologies.

Triggering causes for an ALI (Acute Lung Injury) including ARDS can, for example, be [cited in accordance with Harrison's Principles of Internal Medicine 10th Ed. 1983 McGraw-Hill Int. Book Comp.] diffuse pulmonary infections (e.g. due to viruses, bacteria, fungi), aspiration of, for example, gastric juice or in the case of near-drowning, inhalation of toxins or irritants (e.g. chlorine gas, nitrogen oxides, smoke), direct or indirect trauma (e.g. multiple fractures or pulmonary contusion), systemic reactions to inflammations outside the lung (e.g. hemorrhagic pancreatitis, gram-negative septicemia), transfusions of high blood volumes or alternatively after cardiopulmonary bypass.

Presently, the therapy of ARDS mainly consists in the earliest possible application of different forms of ventilation (e.g. raising of the oxygen concentration of the respiratory air) up to extracorporeal membrane oxygenation. The specific use of various ventilation techniques has only led to a small lowering of mortality and including the risk of damaging the lungs by ventilation with pressure and high $FIO_2$ (Fraction of Inspired Oxygen; proportion of oxygen in the respiratory air). In particular, ARDS patients whose lungs have been damaged by ventilation need even higher pressures and higher $FIO_2$ to obtain an adequate oxygenation of the blood.

Surfactant abnormalities of differing severity are also reported for a number of other disease conditions, for example in obstructive pulmonary disorders such as asthma, bronchiolitis, COPD and after lung transplantation or alternatively after cardiopulmonary bypass [survey, see, for example, M. Griese Eur. Respir. J. 1999; 13: 1455-1467]. As reviewed by Hohlfeld et al. [Hohlfeld J et al. Eur Respir J 1997, 10: 482-91], smoking plays a role not only in the pathogenesis of the alveolar destruction and airway inflammation known for COPD patients, but also in altering surfactant composition and function.

For many years, it has proven suitable to treat IRDS by introducing pulmonary surfactant preparations into the lungs of the children concerned. It is known from pilot studies that pulmonary surfactant preparations are also clinically active in ALI including ARDS.

WO0027360 discloses a treatment set for the treatment of IRDS or ARDS comprising a first container containing a pulverulent pulmonary surfactant preparation and a second container containing a pulverulent surfactant preparation.

WO0158423 discloses the use of a pulmonary surfactant preparation for the production of a medicament for the prophylaxis or treatment of chronic diseases, such as COPD, asthma, cystic fibrosis, pulmonary fibrosis, pulmonary degeneration, chronic bronchitis or pulmonary emphysema.

Combinations of pulmonary surfactant with other therapeutically effective compounds are known from prior art WO 9609831 indicates compositions for the treatment of ARDS and IRDS which contain a glucocorticosteroid and lung surfactant WO 9835683 relates to a composition for the treatment of IRDS and ARDS comprising N-(3,5-dichloro-pyrid-4-yl)-3-cyclopropylmethoxy-4-difluoromethoxybenzamide and lung surfactant. WO 9966926 relates to a composition for the treatment of IRDS and ARDS comprising 4-(2,6-dichloroanilino)-3-thiopheneacetic add or 2-(2-hydroxyethoxy)ethyl 4-(2,6-dichoroanilino)-3-thiopheneacetate and lung surfactant WO 03011316 relates to a combination of a selective COX-2 inhibitor and lung surfactant.

A whole series of PDE5 inhibiting substances are known from the prior art and are described as potent and effective substances for the treatment of erectile dysfunction and pulmonary hypertension. For example, EP1223170 discloses a PDE5 inhibitor and its use for the prophylaxis or treatment of pulmonary hypertension and asthma.

SUMMARY OF THE INVENTION

The invention relates to pharmaceutical compositions comprising a pulmonary surfactant in combination with a PDE5 inhibitor and methods for preventing or reducing the onset of symptoms of a disease in which pulmonary surfactant malfunction and/or phosphodiesterase 5 (PDE5) activity is detrimental, and methods for treating or reducing the severity of a disease in which pulmonary surfactant malfunction and/or phosphodiesterase 5 (PDE5) activity is detrimental.

In particular it relates to pharmaceutical compositions and methods for treating a disease mediated by pulmonary surfactant malfunction and/or phosphodiesterase 5 (PDE5) activity by administering a pulmonary surfactant in combination with a PDE5 inhibitor.

In this connection, it is the object of the present invention to make available a certain therapeutic, which fulfills the following conditions:

Reducing pulmonary surfactant malfunction
Remachting ventilation/perfusion mismatch
Ameliorating oxygenation
Improving physical performance.

It has now been found that the combined use of a pulmonary surfactant and a PDE5 inhibitor fulfills at least one of the abovementioned conditions. Preferably, the combined use of a pulmonary surfactant and a PDE5 inhibitor fulfills at least two of the abovementioned conditions. It is particularly preferred that the combined use of a pulmonary surfactant and a PDE5 inhibitor fulfills at least three of the abovementioned conditions.

Accordingly, the invention relates in a first aspect to the combined use of a pulmonary surfactant and a PDE5 inhibitor for preventing or reducing the onset of symptoms of a disease, or treating or reducing the severity of a disease in a patient in need thereof, in which disease pulmonary surfactant malfunction and/or phosphodiesterase 5 (PDE5) activity is detrimental.

In another aspect of present invention, there is provided the use of a combination of a pulmonary surfactant and a PDE5 inhibitor for the preparation of a medicament for preventing or reducing the onset of symptoms of a disease, or treating or reducing the severity of a disease in a patient in need thereof, in which disease pulmonary surfactant malfunction and/or phosphodiesterase 5 (PDE5) activity is detrimental.

In another aspect of present invention, there is provided a method for preventing or reducing the onset of symptoms of a disease in which pulmonary surfactant malfunction and/or phosphodiesterase 5 (PDE5) activity is detrimental, or treating or reducing the severity of a disease in which pulmonary surfactant malfunction and/or phosphodiesterase 5 (PDE5) activity is detrimental by administering to a patient in need thereof an effective amount of (1) a pulmonary surfactant and (2) a PDE5 inhibitor.

In another aspect of present invention, there is provided a method for preventing or reducing the onset of symptoms of a disease in which pulmonary surfactant malfunction and/or phosphodiesterase 5 (PDE5) activity is detrimental, or treating or reducing the severity of a disease in which pulmonary surfactant malfunction and/or phosphodiesterase 5 (PDE5) activity is detrimental by administering to a patient in need thereof a fixed combination of an effective amount of a pulmonary surfactant and a PDE5 inhibitor, and optionally a pharmaceutically acceptable carrier.

In another aspect of present invention, there is provided a method for preventing or reducing the onset of symptoms of a disease in which pulmonary surfactant malfunction and/or phosphodiesterase 5 (PDE5) activity is detrimental, or treating or reducing the severity of a disease in which pulmonary surfactant malfunction and/or phosphodiesterase 5 (PDE5) activity is detrimental by administering to a patient in need thereof a free combination of an effective amount of a pulmonary surfactant and a PDE5 inhibitor and optionally a pharmaceutically acceptable carrier.

In another aspect of this invention, there is provided a method for preventing or reducing the onset of symptoms of a disease in which pulmonary surfactant malfunction and/or phosphodiesterase 5 (PDE5) activity is detrimental, or treating or reducing the severity of a disease in which pulmonary surfactant malfunction and/or phosphodiesterase 5 (PDE5) activity is detrimental by administering to a patient in need thereof simultaneously an effective amount of (1) a pulmonary surfactant and (2) a PDE5 inhibitor.

In another aspect the invention relates to a method for preventing or reducing the onset of symptoms of a disease in which pulmonary surfactant malfunction and/or phosphodiesterase 5 (PDE5) activity is detrimental, or treating or reducing the severity of a disease in which pulmonary surfactant malfunction and/or phosphodiesterase 5 (PDE5) activity is detrimental by administering to a patient in need thereof in succession, dose in time or remote in time, in any order whatever to a patient in need thereof an effective amount of (1) a pulmonary surfactant and (2) a PDE5 inhibitor.

In another aspect of present invention, there is provided the use of a combination of a pulmonary surfactant and a PDE5 inhibitor for the preparation of a medicament for preventing or reducing the onset of symptoms of a disease, or treating or reducing the severity of a disease in a patient in need thereof, whereby the disease is selected from the group consisting of COPD, bronchus, bronchial asthma, pulmonary fibroses, emphysema, interstitial pulmonary disorders, pneumonia, ALI, ARDS, IRDS and asthma bronchiale.

The invention additionally relates to a method for preparing a pharmaceutical composition which is effective for preventing or reducing the onset of symptoms of a disease in which pulmonary surfactant malfunction and/or phosphodiesterase 5 (PDE5) activity is detrimental, or treating or reducing the severity of a disease in which pulmonary surfactant malfunction and/or phosphodiesterase 5 (PDE5) activity is detrimental, which method comprises mixing an effective amount of a pulmonary surfactant and a PDE5 inhibitor with a pharmaceutically acceptable carrier.

In another aspect of present invention there is provided a pharmaceutical composition comprising a pulmonary surfactant in a fixed combination with a PDE5 inhibitor and optionally a pharmaceutically acceptable carrier for preventing or reducing the onset of symptoms or treating or reducing the severity of a disease in which pulmonary surfactant malfunction and/or phosphodiesterase 5 (PDE5) activity is detrimental.

In another aspect of present invention there is provided a pharmaceutical composition comprising a pulmonary surfactant in a free combination with a PDE5 inhibitor for preventing or reducing the onset of symptoms or treating or reducing the severity of a disease in which pulmonary surfactant malfunction and/or phosphodiesterase 5 (PDE5) activity is detrimental.

In another aspect of present invention there is provided the use of a pharmaceutical composition comprising a pulmonary surfactant with a PDE5 inhibitor and optionally a pharmaceutically acceptable carrier for preventing or reducing the onset of symptoms or treating or reducing the severity of a disease, whereby the disease is selected from the group consisting of COPD, bronchitis, bronchial asthma, pulmonary fibroses, emphysema, interstitial pulmonary disorders, pneumonia, ALI, ARDS, IRDS or asthma bronchiale.

DETAILED DESCRIPTION OF THE INVENTION

The combination therapy, which is the subject matter of present invention, comprises administering a pulmonary surfactant with a PDE5 inhibitor to prevent the onset of a disease in which pulmonary surfactant malfunction and/or phosphodiesterase 5 (PDE5) activity is detrimental.

The invention thus relates to the combined use of a pulmonary surfactant and a PDE5 inhibitor in pre venting the symptoms of, or treating a disease in which pulmonary surfactant malfunction and/or phosphodiesterase 5 (PDE5) activity is detrimental.

The pulmonary surfactant useful in this invention may be any compound or pulmonary surfactant preparation that is known to have the same surface-active properties as natural pulmonary surfactant; natural pulmonary surfactant reduces, for example, the surface tension in the alveoli.

A simple and rapid in vitro test with which the surface activity of pulmonary surfactant can be determined is, for example, the so-called Wilhelmy balance [Goerke, J. Biochim. Biophys. Acta, 344: 241-261 (1974), King R. J. and Clements J. A., Am. J. Physicol. 223: 715-726 (1972)]. This method gives information on the pulmonary surfactant quality, measured as the action of a pulmonary surfactant in achieving a surface tension of almost zero mN/m. Another measuring device for determining the surface activity of pulmonary surfactant is the pulsating bubble surfactometer [Possmayer F. et al., Prog. Resp. Res., Ed. v. Wichert, Vol. 18: 112-120 (1984)]. The activity of a pulmonary surfactant preparation can also be determined by means of in vivo tests, for example as described by Häfner et al. [D. Häfner et al.: Effects of rSP-C surfactant on oxygenation and histology in a rat lung lavage model of acute lung injury. Am. J. Respir. Crit. Care Med. 1998, 158: 270-278].

A group of known pulmonary surfactant preparations and their modifications that may be usefully as pulmonary surfactant employed in the present invention include pulmonary surfactant preparations having the function of natural pulmonary surfactant. Preferred pulmonary surfactant preparations are those which, for example, have activity in the tests described above. Particularly preferred pulmonary surfactant preparations are those which exhibit increased activity in such a test in comparison with natural, in particular human, pulmonary surfactant. In this context, these can be compositions which only contain phospholipids, but also compositions which, apart from the phospholipids, inter alia additionally contain pulmonary surfactant protein.

Preferred phospholipids according to the invention are dipalmitoylphosphatidylcholine (DPPC), palmitoyloleylphosphatidylglycerol (POPG) and/or phosphatidylglycerol (PG). Particularly preferably, the phospholipids are mixtures of various phospholipids, in particular mixtures of dipalmitoylphosphatidyicholine (DPPC) and palmitoyloleylphosphatidylglycerol (POPG), preferably in the ratio from 7 to 3 to 3 to 7.

Commercial products which may be mentioned as pulmonary surfactant preparations are
CUROSURF® (INN: PORACTANT ALFA) (Serono, Pharma GmbH, Unterschleißheim), a natural surfactant from homogenized porcine lungs;
SURVANTA® (INN: BERACTANT) (Abbott GmbH, Wiesbaden), extract of bovine lungs;
ALVEOFACT® (INN: BOVACTANT) (Boehringer Ingelheim), extract of bovine lungs;
EXOSURF® (INN: COLFOSCERIL PALMITATE) (Glaxo SmithKline), a synthetic phospholipid containing excipients;
SURFACTEN® (INN: SURFACTANT-TA) (Mitsubishi Pharma Corporation), a pulmonary surfactant extracted from bovine lungs;
INFASURF® (INN: CALFACTANT) (Forest Pharmaceutcals), a surfactant extracted from calf lungs;
ALEC® (INN: PUMACTANT) (Britannia Pharmaceuticals), an artificial surfactant of DPPC and PG; and
BLES® (BLES Biochemical Inc.), a bovine lipid extract surfactant.

Suitable pulmonary surfactant proteins are both the proteins obtained from natural sources, such as pulmonary lavage or extraction from amniotic fluid, and the proteins prepared by genetic engineering or chemical synthesis. According to the invention, in particular the pulmonary surfactant proteins designated by SP-B (Surfactant Protein-B) and SP-C (Surfactant Protein-C) and their modified derivatives are of interest. The amino add sequences of these pulmonary surfactant proteins, their isolation or preparation by genetic engineering are known (e.g. from WO 8603408, EP 0251449, WO 8904326, WO 8706943, WO 8803170, WO 9100871, EP 0368823 and EP 0348967). Modified derivatives of the pulmonary surfactant proteins designated by SP-C, which differ from human SP-C by the replacement of a few amino acids, are described, for example, in WO 9118015 and WO 9532992. Particularly to be emphasized in this connection are the recombinant SP-C (rSP-C) derivatives which are disclosed in WO 9532992, in particular those which differ from human SP-C in positions 4 and 5 by the substitution of cysteine by phenylalanine and in position 32 by the substitution of methionine by isoleucine [designated herein as rSP-C (FF/I) or LUSUPULTIDE (INN) or VENTICUTE®]. Modified derivatives of pulmonary surfactant proteins are also understood as meaning those proteins which have a completely originally designed amino add sequence with respect to their pulmonary surfactant properties, such as are described in EP 0593094 and WO 9222315. Preferably, the polypeptide KL4 (INN: SINAPULTIDE, SURFAXIN®) may be mentioned in this connection. The name pulmonary surfactant protein, according to the invention, also comprises mixtures of different pulmonary surfactant proteins. In EP 0100910, EP 0110498, EP 0119056, EP 0145005 and EP 0286011 phospholipid compositions with and without pulmonary surfactant proteins are described which are likewise suitable as components of the preparations.

As further constituents which can be present in pulmonary surfactant preparations, fatty adds such as palmitic add may be mentioned. The pulmonary surfactant preparations can also contain electrolytes such as calcium, magnesium and/or sodium salts (for example calcium chloride, sodium chloride and/or sodium hydrogencarbonate) in order to establish an advantageous viscosity. Preferred pulmonary surfactant preparations according to the invention contain 80 to 95% by weight of phospholipids, 0.5 to 3.0% by weight of pulmonary surfactant proteins, 3 to 15% by weight of fatty acid, preferably palmitic acid, and 0 to 3% by weight of calcium chloride.

The pulmonary surfactant preparations are prepared by processes known per se and familiar to the person skilled in the art, for example as described in WO 9532992. According to the invention, the pulmonary surfactant preparations are preferably lyophilized and in particular spray-dried pulmonary surfactant preparations. Lyophilized preparations are disclosed, for example, in WO 9735882, WO 9100871 and DE 3229179. WO 9726863 describes a process for the preparation of powdered pulmonary surfactant preparations by spray drying. According to the invention, preparations prepared in this way are preferred.

The PDE5 inhibitors useful in this invention may be any compound that is known to inhibit the PDE5 enzyme or which is discovered to act as a PDE5 inhibitor, and which is only or essentially only a PDE5 inhibitor, not compounds which inhibit to a degree of exhibiting a therapeutic effect other members of the PDE family as well as PDE5.

A group of PDE5 inhibitors that may be usefully employed in the present invention include a compound selected from SY-39: 4-Methyl-5-(4-pyridinyl)thiazole-2-carboxamide, the preparation of these compounds and their pharmaceutically acceptable salts as well as their use as PDE5 inhibitors is disclosed in the patent application EP 0199968;

DIPYRIDAMOL: 2,2',2'',2'''-[(4,8-dipiperidinopyrimido[5,4-]pryimidine-2,6-diyl)-dinitrilo]-tetraethanol, the preparation of these compounds and their pharmaceutically acceptable salts as well as their use as PDE5 inhibitors is disclosed in the patent application DE1116676;

SKF-96231: 2-(2-propoxyphenyl)purin-6(1H)-one2-(2-propoxyphenyl)-1,7-dihydro-5H-purin-6-one, the preparation of these compounds and their pharmaceutically acceptable salts as well as their use as PDE5 inhibitors is disclosed in the patent application EP 0293063;

ER-21355: 1-[6-chloro-4-(3,4-methylenedioxybenzylamino)quinazolin-2-yl]-piperidine-4-carboxylic acid, the preparation of these compounds and their pharmaceutically acceptable salts as well as their use as PDE5 inhibitors is disclosed in the patent application WO 9307124;

SCH-51866: (+)-cis-5-methyl-2-[4-trifluoromethyl)benzyl]-3,4,5,6a,7,8,9-octahydrocyclopent[4,5]imidazo[2,1-b]purin-4-one, the preparation of these compounds and their pharmaceutically acceptable salts as well as their use as PDE5 inhibitors is disclosed in the patent application WO 9419351;

A-02131-1: 5-[6-fluoro-1-phenylmethyl)-1H-indazol-3-yl]-2-furan-methanol, the preparation of these compounds and their pharmaceutically acceptable salts as well as their use as PDE5 inhibitors is disclosed in the patent application EP 0667345;

SCH-59498: cis-2-hexyl-5-methyl-3,4,5,6a,7,8,9,9a-octahydrocyclopent[4,5]imidazo-[2,1-b]purin-4-one, the preparation of these compounds and their pharmaceutically acceptable salts as well as their use as PDE5 inhibitors is disclosed in the patent application WO 9119717;

E-4010: 4-(3-chloro-4-methoxybenzylamio)-1-(4-hydroxypiperidin-1-yl)-phthalazine-6-carbonitrile, the preparation of these compounds and their pharmaceutically acceptable salts as well as their use as PDE5 inhibitors is disclosed in the patent application WO 9605176;

TADALAFIL: (6R,12aR)-2,3,6,7,12,12a-hexahydro-2-methyl-6-(3,4-methylenedioxy-phenyl)-pyrazino[2',1': 6,1]pyrido[3,4-b]indole-1,4-dione, the preparation of these compounds and their pharmaceutically acceptable salts as well as their use as PDE5 inhibitors is disclosed in the patent application WO 9519978;

VARDENAFIL 2-[2-ethoxy-5-(4-ethylpiperazin-1-ylsulfonyl)phenyl]methyl-7-propylimidazo[5,1-f][1,2,4]triazin-4-(3H)-one, the preparation of these compounds and their pharmaceutically acceptable salts as well as their use as PDE5 inhibitors is disclosed in the patent application WO 9924433;

UK-343664: 1-ethyl-4-[[3-[3-ethyl-4,7-dihydro-7-oxo-2-(2-pyridinylmethyl)-2H-pyrazolo[4,3-d]pyrimidin-5-yl]-4-propoxyphenyl]sulfonyl]-piperazine, the preparation of these compounds and their pharmaceutically acceptable salts as well as their use as PDE5 inhibitors is disclosed in the patent application WO 9849166;

T-0156: 2-(2-methylpydidin-4-ylmethyl)-1-oxo-8-(2-pyrimidinylmethoxy)-4-(3,4,5-trimethoxyphenyl)-1,2-dihydro[2,7]naphthyridine-3-carboxylic acid methyl ester, the preparation of these compounds and their pharmaceutically acceptable salts as well as their use as PDE5 inhibitors is disclosed in the patent application WO 0012503;

DA-8159: 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide, the preparation of these compounds and their pharmaceutically acceptable salts as well as their use as PDE5 inhibitors is disclosed in the patent application WO 0027848;

FR-181074: 1-(2-chlorobenzyl)-3-isobutyryl-2-propylindole-6-carboxamide, the preparation of these compounds and their pharmaceutically acceptable salts as well as their use as PDE5 inhibitors is disclosed in the patent application WO 9632379;

FR-226807: N-(3,4-dimethoxybenzyl)-2-[2-hydroxy-1(R)-methylethylamino]-5-nitrobenzamide, the preparation of these compounds and their pharmaceutically acceptable salts as well as their use as PDE5 inhibitors is disclosed in the patent application WO 9954284;

SILDENAFIL: 5-[2-ethoxy-5-(4-methyl-1-piperazinylsulfonyl)phenyl]-1-methyl-3-n-propyl-1,6-dihydro-7H-pyrazolo[4,3-d]pyrimidin-7-one, the preparation of these compounds and their pharmaceutically acceptable salts as well as their use as PDE5 inhibitors is disclosed in the patent application EP 0463756;

KF-31327: 3-ethyl-8-[2-[4-(hydroxymethyl)piperidin-1-yl]benzylamino]-2,3-dihydro-1H-imidazo[4,5-g]quinazoline-2-thione, the preparation of these compounds and their pharmaceutically acceptable salts as well as their use as PDE5 inhibitors is disclosed in the patent application WO 9808848;

T-1032: 2-(4-aminophenyl)-1-oxo-7-(2-pyridinylmethoxy)-4-(3,4,5-trimethoxyphenyl)-1,2-dihydroisoquinoline-3-carboxylic acid methyl ester, the preparation of these compounds and their pharmaceutically acceptable salts as well as their use as PDE5 inhibitors is disclosed in the patent application WO 9838168;

FR-229934: pentane-1-sulfonic acid[1-[3-(3,4-dichlorobenzy)-2-methyl-3H-benzoimidazol-5-yl]-methanoyl}-amide, the preparation of these compounds and their pharmaceutically acceptable salts as well as their use as PDE5 inhibitors is disclosed in the patent application WO 9900373;

BMS-263504: 1-[[3-(7,8-dihydro-8-oxo-1H-imidazo[4,5-g]quinazolin-6-yl)-4-propoxyphenyl]sulfonyl]-4-methylpiperazine, the preparation of these compounds and their pharmaceutically acceptable salts as well as their use as PDE5 inhibitors is disclosed in the patent application WO 9964004;

WIN-65579: 1-cyclopentyl-6-(3-ethoxy-4-pyridinyl)-3-ethyl-1,7-dihydro-4H-pyrazolo[3,4-d]pyrimidin-4-one, the preparation of these compounds and their pharmaceutically acceptable salts as well as their use as PDE5 inhibitors is disclosed in the patent application U.S. Pat. No. 5,294,612;

UK-371800: 3-ethyl-5-[5-(4-ethylpiperazin-1-ylsulfonyl)-2-[2-methoxy-1(R)-methyl-ethoxy]pyridin-3-yl]-2-methyl-6,7-dihydro-2H-pyrazolo[4,3-d]-pryimidin-7-one, the preparation of these compounds and their pharmaceutically acceptable salts as well as their use as PDE5 inhibitors is disclosed in the patent application WO 9954333;

BF/GP-385: 2-(1H-imidazol-1-yl)-6-methoxy-4-(2-methoxyethylamino)-quinazoline, the preparation of these compounds and their pharmaceutically acceptable salts as well as their use as PDE5 inhibitors is disclosed in the patent application EP 0579496;

CP-248: (1Z)-N-benzyl-2-[6-fluoro-2-methyl-3-(3,4,5-trimethoxybenzylidene)-3H-inden-1-yl]-acetamide, the preparation of these compounds and their pharmaceutically acceptable salts as well as their use as PDE5 inhibitors is disclosed in the patent application WO 9747303;

ZAPRINAST: 3,6-dihydro-5-(o-propoxyphenyl)-7H-s-triazolo[4,5-d]pyrimidin-7-one, the preparation of these compounds and their pharmaceutically acceptable salts as well as their use as PDE5 inhibitors is disclosed in the patent application DE 2162096; and VESNARINONE: 3,4-dihydro-6-[4-(3,4-dimethoxybenzoyl)-1-piperazinyl]-2(1H)-quinolinone, the preparation of these compounds and their pharmaceutically acceptable salts as well as their use as PDE5 inhibitors is disclosed in the patent application DE 3142982.

Salts encompassed within the term "pharmaceutically acceptable salts" refer to non-toxic salts of the compounds which are generally prepared by reacting a free base with a suitable organic or inorganic acid or by reacting the add with a suitable organic or inorganic base. Particular mention may be made of the pharmaceutically acceptable inorganic and organic adds customarily used in pharmacy. Those suitable are in particular water-soluble and water-insoluble acid addition salts with acids such as, for example, hydrochloric acid, hydrobromic acid, phosphoric add, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric add, embonic add, stearic add, toluenesulfonic acid, methanesulfonic acid or 1-hydroxy-2-naphthoic add, the adds being employed in salt preparation—depending on whether it is a mono- or polybasic acid and depending on which salt is desired—in an equimolar quantitative ratio or one differing therefrom.

As examples of salts with bases are mentioned the lithium, sodium, potassium, calcium, aluminium, magnesium, titanium, ammonium; meglumine or guanidinium salts, here, too, the bases being employed in salt preparation in an equimolar quantitative ratio or one differing therefrom.

It is understood that the active compounds and their pharmaceutically acceptable salts mentioned can also be present, for example, in the form of their pharmaceutically acceptable solvates, in particular in the form of their hydrates.

One group of PDE5 inhibitors that is particularly preferred in the present invention [hereinafter referred to as "SELECTED PDE5 INHIBITORs"] consists of TADALAFIL (Cialis®), SILDENAFIL (Viagra®), VARDENAFIL (Levitra®), UK357903, E8010 and TA-1790 and the pharmaceutically acceptable salts of these compounds. Preferred SELECTED PDE5 INHIBITORs are TADALAFIL (Cialis®), SILDENAFIL (Viagra®) AND VARDENAFIL (Levitra®) and the pharmaceutically acceptable salts of these compounds. Particularly preferred is SILDENAFIL (Viagra®) and the pharmaceutically acceptable salt of thereof.

"Diseases in which pulmonary surfactant malfunction and/or phosphodiesterase 5 (PDE5) activity is detrimental" which may be mentioned are in particular disorders of varying origin with a pulmonary surfactant deficiency component and a mismacht component. Diseases which may be mentioned as examples are chronic obstructive pulmonary disease (COPD), bronchitis, bronchial asthma, pulmonary fibroses, emphysema, interstitial pulmonary disorders, pneumonia, ALI (Acute Lung Injury), ARDS (Adult Respiratory Distress Syndrome), IRDS (Infant Respiratory Distress Syndrome) and asthma bronchiale. Preferred examples are COPD, ALI, ARDS, IRDS and asthma bronchiale.

The phrase "pulmonary surfactant deficiency component" refers to the disease component characterized by a functional impairment of the surface-active properties of natural pulmonary surfactant to reduce, for example, the surface tension in the alveoli. In particular it refers to the disease component characterized by the destruction of natural pulmonary surfactant and to the consequential loss of the surface-active properties of natural pulmonary surfactant.

The phrase "a mismatch component" refers to the disease component characterized 1. by a more or less pronounced collapse of the alveolar gas exchange function resulting in hypoxaemia (deterioration in gas exchange with decrease in the oxygen content of the patient's blood), wasted perfusion (uneconomical perfusion of unventilated areas) and wasted ventilation (uneconomical ventilation of poorly perfused areas) and/or
2. by more or less pronounced collapse in perfusion of skeletal muscles resulting in wasted perfusion of unstressed muscle groups to the detriment of perfusion of stressed muscle groups.

In accordance with present invention, the mismatch component of a disease leads to a limitation in the patients performance due to a deficient oxygen supply to the muscles in combination with a "squandering" of cardiorespiratory reserves and thus results of a limitation on muscular performance. The clinical symptoms are a limitation on performance and exercise-dependent or permanent dyspnoea In accordance to present invention, regulation of the "perfusion/demand matching" in skeletal muscles takes place in analogy to the lung through local release of endogenous vasodilators (especially NO/cGMP). The demand-oriented perfusion is in favor of the stressed muscle groups (muscular selectivity), and within the muscle groups in favor of the specifically stressed fibre types (intramuscular selectivity). The type of stress, duration of stress and level of stress thus determine under physiological conditions the specific perfusion profiles in each case. Various inflammatory disorders (e.g. COPD) may lead to a perfusion/demand mismatch. The consequence is wasted perfusion of unstressed muscle groups to the detriment of perfusion of stressed muscle groups, with the result of a limitation on muscular performance.

In accordance to present invention, the phrase "rematching" refers to a mechanism by which a mismatch is alleviated; vessels in the pulmonary circulation are dilated and, at the same time, the blood flow within the lung is redistributed in favor of the well-ventilated areas. This mechanism leads to an improvement in the gas exchange function both at rest and during physical exercise. It can be stated that PDE5 inhibitors are able to enhance, in the sense of physiological adaptation of ventilation and perfusion, the necessary vasodilatations specifically in the well-ventilated regions in that they accentuate the physiological inhomogeneity of cGMP distribution in the lung and thus promote rematching. Gas exchange is intensified and the oxygen supply is improved by this mechanism. Rematching also refers to an alleviation of a "perfusion/demand matching" in skeletal muscles—the blood flow is redistributed in favor of the stressed muscle groups (muscular selectivity), and within the muscle groups in favor of the specifically stressed fibre types (intramuscular selectivity).

The phrase "combined use" (or "combination") embraces the administration of a pulmonary surfactant and a PDE5 inhibitor as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combined use" generally is not intended to encompass the administration of two of these therapeutic agents as part of separate monotherapy regimens that incidentally and arbitrarily result in the combinations of the present invention.

"Combined use" or "combination" within the meaning of the present invention is to be understood as meaning that the individual components of the combination can be administered simultaneously (in the form of a combination medicament—"fixed combination") or more or less simultaneously, respectively in succession (from separate pack units—"free combinations", directly in succession or else alternatively at a relatively large time interval) in a manner which is known per se and customary. As an example, one therapeutic agent could be taken in the morning and one later in the day. Or in another scenario, one therapeutic agent could be taken once daily and the other twice weekly. It is understood, that if individual components are administered directly in succession, the delay in administering the second component should not be such as to lose the beneficial therapeutic effect of the combination.

It is to be understood that present invention covers all combinations of particular and preferred aspects of the invention described herein. Thus, present invention clearly refers to all compounds or preparations mentioned herein as examples of a pulmonary surfactant and to all compounds mentioned herein as a PDE5 inhibitor and to all possible consequential combinations. In particular, combinations which may be mentioned as preferred examples of a combination of a pulmonary surfactant and a PDE5 inhibitor are a combination of SILDENAFIL and LUSUPULTIDE,
a combination of TADALAFIL and LUSUPULTIDE,
a combination of VARDENAFIL and LUSUPULTIDE,
a combination of SILDENAFIL and SINAPULTIDE,
a combination of TADALAFIL and SINAPULTIDE,
a combination of VARDENAFIL and SINAPULTIDE,
a combination of SILDENAFIL and PORACTANT ALFA,
a combination of TADALAFIL and PORACTANT ALFA,
a combination of VARDENAFIL and PORACTANT ALFA,
a combination of SILDENAFIL and BERACTANT,
a combination of TADALAFIL and BERACTANT,
a combination of VARDENAFIL and BERACTANT,
a combination of SILDENAFIL and BOVACTANT,
a combination of TADALAFIL and BOVACTANT,
a combination of VARDENAFIL and BOVACTANT,
a combination of SILDENAFIL and COLFOSCERIL PALMITATE,
a combination of TADALAFIL and COLFOSCERIL PALMITATE,
a combination of VARDENAFIL and COLFOSCERIL PALMITATE,
a combination of SILDENAFIL and SURFACTANT-TA,
a combination of TADALAFIL and SURFACTANT-TA,
a combination of VARDENAFIL and SURFACTANT-TA,
a combination of SILDENAFIL and CALFACTANT,
a combination of TADALAFIL and CALFACTANT, and
a combination of VARDENAFIL and CALFACTANT.

Particularly preferred examples of a combination of a pulmonary surfactant and a PDE5 inhibitor are a combination of SILDENAFIL and LUSUPULTIDE, a combination of TADALAFIL and LUSUPULTIDE, and a combination of VARDENAFIL and LUSUPULTIDE.

More or less simultaneous administration of each therapeutic agent can be effected by, for example, intratracheally or intrabronchially administration to the subject in need thereof either as an instillation of the dissolved, liquid therapeutic agents, or as an aerosolised solution or as a dry powder having a fixed ratio of each therapeutic agent.

Administration of each therapeutic agent in succession, close in time or remote in time, can be effected by any appropriate route, including, but not limited to, intratracheal or intrabronchial instillation, oral routes, intravenous routes, intramuscular routes, and direct absorption or through mucous membrane tissues. The therapeutic agents can be administered by the same route or by different routes. For example, a first therapeutic agent of the combination selected may be administered by intratracheal or intrabroncheal instillation while the other therapeutic agent of the combination may be administered orally, intravenously, intratracheally, intrabroncheally, sublingually, intraperetoneally, or subcutaneously. The sequence in which the therapeutic agents are administered is not narrowly critical.

The most preferred route of administration of a pulmonary surfactant is the intratracheally or intrabronchially route by instillation in liquid form or as aerosolised solution or as dry powder.

Dry powder formulations of pulmonary surfactants are preferably, prepared by the spray drying process as described in WO 9726863.

The most preferred route of administration of a PDE5 inhibitor is the oral route. In another preferred embodiment the PDE5 inhibitor administered by intravenous infusion or injection. In a further embodiment the PDE5 inhibitor is administered by intramuscular or subcutaneous injection. Other routes of administration are also contemplated, including intranasal and transdermal routes, by inhalation and by intratracheally or intrabronchially instillation.

In case of pharmaceutical compositions, which are intended for oral administration, the therapeutic agent(s) are formulated to give medicaments according to processes known per se and familiar to the person skilled in the art. The therapeutic agents are employed as medicament, preferably in combination with suitable pharmaceutical carrier, in the form of tablets, coated tablets, capsules, caplets, emulsions, suspensions, syrups or solutions, the therapeutic agent content advantageously being between 0.1 and 95% by weight and, by the appropriate choice of the carrier, it being possible to achieve a pharmaceutical administration form precisely tailored to the therapeutic agent(s) and/or to the desired onset of action (e.g. a sustained-release form or an enteric form).

The person skilled in the art is familiar on the basis of his/her expert knowledge which carriers or excipients are suitable for the desired pharmaceutical formulations. In addition to solvents, gel-forming agents, tablet excipients and other active compound carriers, it is possible to use, for example, anti oxidants, dispersants, emulsifiers, antifoams, flavor corrigents, preservatives, solubilzers, colorants or permeation promoters and complexing agents (e.g. cyclodextrins).

The therapeutic agent(s) of the present invention can be administered by a variety of methods known in the art, although for many therapeutic applications, the preferred route of administration is a free combination of a pulmonary surfactant and a PDE5 inhibitor whereby the pulmonary surfactant is administered as a dry powder by inhalation or by intratracheal or intrabronchial instillation of a liquid and the PDE5 inhibitor is administered orally. For some therapeutic application it may be preferable to administer the pulmonary surfactant and the PDE5 inhibitor in a fixed combination, whereby the preferred route of administration is inhalation of a dry powder formulation or intrabronchial instillation of a liquid formulation.

The therapeutic agent(s) are dosed in an order of magnitude customary for the individual dose. It is more likely possible that the individual actions of the therapeutic agents are mutually positively influenced and reinforced and thus the respective doses on the combined administration of the therapeutic agent(s) may be reduced compared with the norm.

In case of intratracheally or intrabronchial administration of a pulmonary surfactant preparation, it has proven advantageous to administer suspensions or solutions of the preparations according to the invention which contain 10 to 100 mg of phospholipids per ml of suspension. Preferably, the preparations according to the invention are administered per application in such an amount that the amount of phospholipids is between 10 and 400 mg per kilogram of body weight as a rule, administration is carried out 1 to 3 times daily over a period of 1 to 7 days. A process is preferred in which the pulmonary surfactant solution employed contains 0.5 to 2.0 mg of rSP-C (FF/I) per ml of solvent. Particular mention may be made of a process in which the pulmonary surfactant solution employed contains 0.75 to 1.5 mg of rSP-C (FF/I) per ml of solvent.

It has also proven advantageous to administer commercially available pulmonary surfactant preparations in suitable dosages in accordance with dosage regimens cited in accordance with the summary of product characteristics. In case of intratracheally administration of BLES® the daily dose of the phospholipids will likely be in the range of 100-150 mg/kg body weight. Preferably, the daily dose will likely be 135 mg phospholipids/kg body weight in case of intratracheally administration of CALFACTANT the daily dose will likely be 3-6 mL/kg body weight of CALFACTANT which is about 105-210 mg phospholipids and 1.95-3.90 mg Surfactant Protein-B (SP-B) per kg body weight in case of intratracheally administration of SURFACTANT-TA the daily dose will likely be 60-120 mL SURFACTANT-TA per kg body weight. In case of intratracheally administration of PORACTANT ALFA the daily dose will likely be 100-200 mg/kg up to a daily maximum dose of 300-400 mg/kg which is about 70-280 mg phospholipids per kg body weight and 1-4 g hydrophobic proteins (Surfactant Protein-B and Surfactant Protein-C) per kg body weight. IN the case of intratracheally administration of BERACTANT the daily dose will likely be 100-200 mg phospholipids per kg body weight and 4-8 mg hydrophobic proteins (Surfactant Protein-B and Surfactant Protein-C) per kg body weight. In the case of intratracheally administration of COLFOSCERIL PALMITATE the daily dose will likely be 54-162 mg phospholipids per kg body weight.

In case of oral, intravenous or subcutaneous administration of a PDE5 inhibitor, the daily dose will likely be in the range from 0.001 to 3 mg/kg body weight of the subject to be treated, preferably by once daily administration.

Tablet formulations for SILDENAFIL, TADALAFIL and VARDENAFIL are commercially available under the tradenames Viagra®, Cialis® and Levitra® respectively.

Commercially available tablet formulations for SILDENAFIL contain 25, 50 or 100 mg of SILDENAFIL. According to the Summary of Product Characteristics for Viagra®, as a monotherapy the PDE5 inhibitor SILDENAFIL is generally administered orally to adults in a daily dose of 25, 50 or 100 mg.

Commercially available tablet formulations for VARDENAFIL contain 5, 10 or 20 mg of VARDENAFIL. According to the Summary of Product Characteristics for Levitra®, as a monotherapy the PDE5 inhibitor VARDENAFIL is generally administered orally to adults in a daily dose of 5, 10 or 20 mg.

Commercially available tablet formulations for TADALAFIL contain 10 or 20 mg of TADALAFIL. According to the Summary of Product Characteristics for Cialis®, as a monotherapy the PDE5 inhibitor TADALAFIL is generally administered orally to adults in a daily dose of 10 or 20 mg.

Utility

Combinations of present invention may be prescribed to the patient in "patient pack" containing the whole course of treatment in a single package. Patient packs have an advantage over traditional prescriptions, where a pharmacist divides a patient's supply of a pharmaceutical from a bulk supply, in that the patent always has access to the package insert contained in the patient pack, normally missing in traditional prescriptions. The inclusion of a package insert has been shown to improve patient compliance with the physician's instructions and, therefore, lead generally to more successful treatment. It will be understood that the administration of a combination of present invention by means of a single patient pack, or patient packs of each component compound, and containing a package insert instructing the patient to the correct use of the invention is a desirable additional feature of the invention leading to an increased compliance of the patient compared to the administration of each single component.

Another beneficial effect of present invention refers to use of combinations of present invention. It has surprisingly been found that a unexpected therapeutic benefit, particularly a synergistic benefit, in the prevention or reduction of the onset of symptoms of a disease, or in the treatment or reduction of the severity of a disease in a patient in need thereof, in which disease pulmonary surfactant malfunction and/or phosphodiesterase 5 (PDE5) activity is detrimental, can be obtained by using a composition of a pulmonary surfactant and a PDE5 inhibitor. For instance, it is possible by using such a combination to superiorly ameliorate oxygenation in a patient with a disease in which pulmonary surfactant malfunction and/or phosphodiesterase 5 (PDE5) activity is detrimental compared to the use of pulmonary surfactant or a PDE5 inhibitor alone. In particular it has been found that the combined use of a pulmonary surfactant and a PDE5 inhibitor induces a beneficial effect referred to the pulmonary surfactant deficiency component and/or the mismatch component which is significantly greater than that induced by pulmonary surfactant alone or a PDE5 inhibitor alone. Therefore, (1) the amount of the pulmonary surfactant may be significantly reduced when used in a combination with a PDE5 inhibitor, which inter alia significantly reduces costs of the therapy of a patient in need thereof, as pulmonary surfactants are comparatively costly. (2) The frequency of ungratefulness related to the application of a pulmonary surfactant, for example, by instillation may also be reduced compared to the use of a pulmonary surfactant alone.

As another beneficial effect of present combinations, the combined use of a pulmonary surfactant and a PDE5 inhibitor significantly improves patients bodily performance— compared to the use of a pulmonary surfactant alone or a PDE5 inhibitor alone—as the activity of the combination does not only improve oxygenation as known for the single application of a pulmonary surfactant but also reduces the severity of a perfusion/ventilation mismatch of lungs and/or a perfusion/demand mismatch of skeletal muscles. Thus the combined use of a pulmonary surfactant and a PDE5 inhibitor improves (1) ventilation of the lungs, (2) specific perfusion of lungs at sites of adequate ventilation and (3) the demand-oriented perfusion in favor of the stressed muscle groups.

Finally, it as been found that the use of a combination of a pulmonary surfactant and a PDE5 inhibitor significantly reduces the time patients with ARDS or IRDS have to be ventilated, and thus, it is possible by the administration of a combination of a pulmonary surfactant and a PDE5 inhibitor to avoid side effects of ventilation, for example the risk of a nosocomial or pneumonia for the patients can be lowered compared to the use of a pulmonary surfactant alone.

EXAMPLES

Example 1

Fixed Combination of LUSUPULTIDE and TADALAFIL for Dry Powder Inhalation 9.8 g of 1,2-dipalmitoyl-3-sn-phosphatidylcholine, 4.2 g of 1-palmitoyl-2-oleoyl-3-sn-phosphatidylglyce-rolammonium, 0.62 g of TADALAFIL, 0.7 g of palmitic acid, 0.36 g of calcium chloride and 0.28 g of r-SP-C (FF/I) are dissolved in 820 ml of 2-propanol/water (90:10) and spray-dried in a Büchi B 191 laboratory spray-dryer. Spray conditions: drying gas nitrogen, inlet temperature 110° C., outlet temperature 59-61° C. A fine powder is obtained which can be micronized. About 55 mg/kg body weight can be administered intratracheally as a dry powder with an appropriate dry powder inhaler device for a single application.

Example 2

Fixed Combination of LUSUPULTIDE and SILDENAFIL for Intrabronchial Instillation 9.8 g of 1,2-dipalmitoyl-3-sn-phosphatidylcholine, 4.2 g of 1-palmitoyl-2-oleoyl-3-sn-phosphatidylglyce-rolammonium, 0.7 g of palmitic acid, 0.36 g of calcium chloride and 0.28 g of r-SP-C (FF/I) are spray-dried as described in Example 1. 0.79 mg SILDENAFIL is dissolved in 1 mL 0.01 N hydrochloric acid and further diluted with 279 mL 0.9% sodium chloride. The 15.34 g of the surfactant composition are added to this solution and suspended. For a single application in humans 1 m/kg body weight of this suspension can be instilled intrabronchially guided by a bronchoscope.

Example 3

Free Combination of BERACTANT for Intratracheal Instillation and SILDENAFIL for Oral Administration For a single application in humans commercially available BERACTANT (SURVANTA®) is administered intratracheally 100 mg/kg as a suspension in 0.9% sodium chloride containing 25 mg phospholipids per mL (consisting of 11.0-15.5 mg/mL disaturated phosphatidycholine, 0.5-1.75 mg/mL triglycerides, 1.4-3.5 mg/mL free fatty adds, and less than 1.0 mg/mL protein). This application is combined with one or several timed oral administrations of 10 or 20 mg TADALAFIL (commercially available as CIALIS®).

Example 4

Free Combination of PORACTANT Alpha for Intratracheal Instillation and VARDENAFIL for Oral Administration For a single application in humans commercially available PORACTANT alpha (CUROSURF®) is administered intratracheally 100-200 mg/kg. Composition per mL of suspension: phospholipid fraction from porcine lung 80 mg/mL, equivalent to about 74 mg/mL of total phospholipids and 0.9 mg/mL of low molecular weight hydrophobic proteins. This application is combined with one or several timed oral administrations of 10 or 20 mg VARDENAFIL (commercially available as LEVITRA®).

Example 5

Free Combination of LUSUPULTIDE for Intratracheal Instillation and SILDENAFIL for Oral Administration For a single application in humans LUSUPULTIDE is administered by inhalation as a dry powder in a dose of 10-100 mg/kg body weight. Composition per mL of suspension: 10-400 mg/mL of phospholipids and 0.1-4 mg/mL of rSP-C (FF/I). This application is combined with one or several timed oral administrations of 25 or 100 mg SILDENAFIL (commercially available as VIAGRA®).

The invention claimed is:

1. A method for treating or reducing the onset of symptoms of a disease in which pulmonary surfactant malfunction and/or phosphodiesterase 5 (PDE5) activity is detrimental, or treating or reducing the severity of a disease in which pulmonary surfactant malfunction and/or phosphodiesterase 5 (PDE5) activity is detrimental in a patient, comprising administering intratracheally or intrabronchially to a patient in need thereof an effective amount of (1) Lusupultide and (2) Sildenafil or a pharmaceutically acceptable salt thereof wherein the disease in which pulmonary surfactant malfunction and/or phosphodiesterase 5 (PDE5) activity is detrimental is selected from the group consisting of COPD, bronchitis, bronchial asthma, pulmonary fibroses, emphysema, interstitial pulmonary disorders, pneumonia, ALI, ARDS and asthma bronchiale.

2. The method according to claim 1, wherein the (1) Lusupultide and (2) Sildeneafil or a pharmaceutically acceptable salt thereof are administered simultaneously.

3. The method according to claim 1, wherein the (1) Lusupultide and (2) Sildenafil or a pharmaceutically acceptable salt thereof are administered in succession, in any order.

* * * * *

UNITED STATES PATENT AND TRADEMARK OFFICE
CERTIFICATE OF CORRECTION

PATENT NO. : 7,238,664 B2 Page 1 of 1
APPLICATION NO. : 10/560116
DATED : July 3, 2007
INVENTOR(S) : Wollin et al.

It is certified that error appears in the above-identified patent and that said Letters Patent is hereby corrected as shown below:

Column 18, Line 12,
Please delete "ALI, ARDS and asthma bronchiale" and replace with -- ALI, ARDS, IRDS and asthma bronchiale --

Signed and Sealed this

Twenty-third Day of October, 2007

JON W. DUDAS
*Director of the United States Patent and Trademark Office*